US008945011B2

(12) United States Patent
Sheldon et al.

(10) Patent No.: US 8,945,011 B2
(45) Date of Patent: *Feb. 3, 2015

(54) SYSTEMS AND METHODS FOR ACCESSING THE LUMEN OF A VESSEL

(75) Inventors: Jeffery J. Sheldon, League City, TX (US); Kenneth R. Smith, League City, TX (US); Bruce W. Dannecker, League City, TX (US); Joseph M. Lacey, Hartselle, AL (US); Katherine E. Goodwin, Houston, TX (US)

(73) Assignee: Houston Medical Robotics, Inc., Houston, TX (US)

( * ) Notice: Subject to any disclaimer, the term of this patent is extended or adjusted under 35 U.S.C. 154(b) by 396 days.

This patent is subject to a terminal disclaimer.

(21) Appl. No.: 13/080,318

(22) Filed: Apr. 5, 2011

(65) Prior Publication Data

US 2012/0259219 A1 Oct. 11, 2012

(51) Int. Cl.
*A61B 8/00* (2006.01)
*A61B 8/08* (2006.01)
*A61M 25/01* (2006.01)
*A61M 25/09* (2006.01)
*A61B 19/00* (2006.01)
(Continued)

(52) U.S. Cl.
CPC .............. *A61B 8/0841* (2013.01); *A61B 8/4209* (2013.01); *A61B 8/461* (2013.01); *A61B 8/587* (2013.01); *A61M 25/0113* (2013.01); *A61M 25/09041* (2013.01); *A61B 19/201* (2013.01); *A61B 17/3403* (2013.01); *A61B 8/0891* (2013.01); *A61M 25/0111* (2013.01); *A61M 25/065* (2013.01); *A61B 2019/5276* (2013.01); *A61B 2017/3407* (2013.01); *A61B 2017/3413* (2013.01)

USPC .......... 600/437; 600/461; 600/417; 600/464; 604/117; 604/164.01

(58) Field of Classification Search
None
See application file for complete search history.

(56) References Cited

U.S. PATENT DOCUMENTS

| | | | | | |
|---|---|---|---|---|---|
| 4,608,977 | A | * | 9/1986 | Brown | 606/130 |
| 4,638,798 | A | * | 1/1987 | Shelden et al. | 606/130 |
| 4,660,563 | A | * | 4/1987 | Lees | 424/1.69 |

(Continued)

FOREIGN PATENT DOCUMENTS

| | | |
|---|---|---|
| WO | 2006120619 | 11/2006 |
| WO | 2010006335 | 1/2010 |

OTHER PUBLICATIONS

International Search Report and Written Opinion for PCT/US12/32310 dated Aug. 10, 2012.

(Continued)

*Primary Examiner* — Nicholas Evoy
(74) *Attorney, Agent, or Firm* — Winstead PC

(57) ABSTRACT

An apparatus for accessing the lumen of a vessel. The apparatus includes a reusable handheld device and a disposable cartridge. The reusable handheld device includes a imaging device attachment utilized to secure an image capturing instrument, an arm coupled to the imaging device attachment, and a depth scale coupled to the arm, wherein the depth scale provides a scale indicating an insertion depth. The disposable cartridge attaches to the reusable handheld device. The disposable cartridge includes a sheath, needle or guidewire coupled to the disposable cartridge. The sheath or needle extends to the insertion depth when fully advanced, thereby allowing the sheath, needle, or guidewire to access the lumen of a vessel.

11 Claims, 12 Drawing Sheets

(51) Int. Cl.
*A61B 17/34* (2006.01)
*A61M 25/06* (2006.01)

(56) References Cited

U.S. PATENT DOCUMENTS

| | | | | |
|---|---|---|---|---|
| 4,706,665 A * | 11/1987 | Gouda | ............................ | 606/130 |
| 4,733,661 A * | 3/1988 | Palestrant | ...................... | 606/108 |
| 4,899,756 A * | 2/1990 | Sonek | ............................ | 600/461 |
| 5,006,122 A * | 4/1991 | Wyatt et al. | .................... | 606/130 |
| 5,116,345 A * | 5/1992 | Jewell et al. | ................... | 606/130 |
| 5,154,723 A * | 10/1992 | Kubota et al. | ................ | 606/130 |
| 5,163,430 A * | 11/1992 | Carol | ............................. | 600/429 |
| 5,201,742 A * | 4/1993 | Hasson | ......................... | 606/130 |
| 5,269,305 A * | 12/1993 | Corol | ............................. | 600/429 |
| 5,445,166 A * | 8/1995 | Taylor | ........................... | 128/897 |
| 5,483,961 A * | 1/1996 | Kelly et al. | ..................... | 600/429 |
| 5,572,999 A * | 11/1996 | Funda et al. | .................... | 600/118 |
| 5,575,798 A * | 11/1996 | Koutrouvelis | ................ | 606/130 |
| 5,643,286 A * | 7/1997 | Warner et al. | ................. | 606/130 |
| 5,647,373 A | 7/1997 | Paltieli | | |
| 5,817,106 A * | 10/1998 | Real | .............................. | 606/130 |
| 5,871,487 A * | 2/1999 | Warner et al. | ................. | 606/130 |
| 5,950,629 A * | 9/1999 | Taylor et al. | .................... | 128/897 |
| 5,957,933 A * | 9/1999 | Yanof et al. | ..................... | 606/130 |
| 5,980,535 A * | 11/1999 | Barnett et al. | ................. | 606/130 |
| 5,997,471 A * | 12/1999 | Gumb et al. | .................... | 600/102 |
| 6,010,476 A * | 1/2000 | Saadat | ............................ | 604/22 |
| 6,071,288 A * | 6/2000 | Carol et al. | ..................... | 606/130 |
| 6,110,182 A * | 8/2000 | Mowlai-Ashtiani | ........... | 606/130 |
| 6,117,078 A * | 9/2000 | Lysyansky et al. | ............ | 600/437 |
| 6,117,143 A * | 9/2000 | Hynes et al. | .................... | 606/130 |
| 6,120,465 A * | 9/2000 | Guthrie et al. | .................. | 600/587 |
| 6,193,657 B1 * | 2/2001 | Drapkin | ......................... | 600/437 |
| 6,210,417 B1 * | 4/2001 | Baudino et al. | ................ | 606/129 |
| 6,231,526 B1 * | 5/2001 | Taylor et al. | .................... | 600/587 |
| 6,254,532 B1 * | 7/2001 | Paolitto et al. | .................. | 600/201 |
| 6,695,786 B2 * | 2/2004 | Wang et al. | .................... | 600/461 |
| 6,835,193 B2 * | 12/2004 | Epstein et al. | ................. | 604/507 |
| 7,166,075 B2 * | 1/2007 | Varghese et al. | .............. | 600/439 |
| 7,366,561 B2 * | 4/2008 | Mills et al. | ..................... | 600/417 |
| 7,497,863 B2 * | 3/2009 | Solar et al. | ..................... | 606/130 |
| 7,559,935 B2 * | 7/2009 | Solar et al. | ..................... | 606/130 |
| 7,691,103 B2 | 4/2010 | Fernandez et al. | | |
| 7,708,751 B2 * | 5/2010 | Hughes et al. | ................. | 606/172 |
| 7,766,839 B2 | 8/2010 | Rogers et al. | | |
| 7,867,242 B2 * | 1/2011 | Solar et al. | ..................... | 606/130 |
| 7,890,155 B2 | 2/2011 | Burns et al. | | |
| 7,976,469 B2 | 7/2011 | Bonde et al. | | |
| 8,066,644 B2 | 11/2011 | Sarkar et al. | | |
| 8,235,908 B2 | 8/2012 | Roschak et al. | | |
| 2002/0177789 A1 * | 11/2002 | Ferry et al. | ..................... | 600/585 |
| 2003/0233046 A1 * | 12/2003 | Ferguson et al. | .............. | 600/437 |
| 2004/0267121 A1 | 12/2004 | Sarvazyan et al. | | |
| 2006/0111692 A1 * | 5/2006 | Hlavka et al. | ................ | 604/890.1 |
| 2006/0111733 A1 | 5/2006 | Shriver | | |
| 2006/0116904 A1 | 6/2006 | Brem | | |
| 2006/0122627 A1 * | 6/2006 | Miller et al. | .................... | 606/129 |
| 2006/0192319 A1 * | 8/2006 | Solar | ............................. | 264/271.1 |
| 2006/0195119 A1 * | 8/2006 | Mazzocchi et al. | ........... | 606/129 |
| 2007/0073155 A1 * | 3/2007 | Park et al. | ....................... | 600/461 |
| 2007/0135803 A1 | 6/2007 | Belson | | |
| 2007/0137372 A1 * | 6/2007 | Devengenzo et al. | ...... | 74/490.01 |
| 2007/0185485 A1 | 8/2007 | Hauck et al. | | |
| 2007/0233045 A1 | 10/2007 | Weitzner et al. | | |
| 2007/0250078 A1 * | 10/2007 | Stuart | ............................ | 606/130 |
| 2008/0140087 A1 | 6/2008 | Barbagli | | |
| 2008/0146918 A1 | 6/2008 | Magnin et al. | | |
| 2008/0275396 A1 * | 11/2008 | Neerken et al. | ................ | 604/116 |
| 2008/0300491 A1 * | 12/2008 | Bonde et al. | .................... | 600/461 |
| 2009/0093761 A1 * | 4/2009 | Sliwa et al. | ..................... | 604/116 |
| 2009/0105597 A1 | 4/2009 | Abraham | | |
| 2009/0125009 A1 | 5/2009 | Zikorus et al. | | |
| 2009/0247993 A1 * | 10/2009 | Kirschenman et al. | ........... | 606/1 |
| 2009/0270760 A1 * | 10/2009 | Leimbach et al. | .............. | 600/567 |
| 2010/0010505 A1 * | 1/2010 | Herlihy et al. | ................. | 606/130 |
| 2010/0036245 A1 | 2/2010 | Yu et al. | | |
| 2010/0256558 A1 * | 10/2010 | Olson et al. | ................. | 604/95.01 |
| 2012/0197132 A1 | 8/2012 | O'Connor | | |
| 2012/0259220 A1 * | 10/2012 | Sheldon et al. | ................ | 600/439 |
| 2012/0259221 A1 * | 10/2012 | Sheldon et al. | ................ | 600/439 |

OTHER PUBLICATIONS

International Search Report and Written Opinion for PCT/US12/32346 dated Aug. 3, 2012.

International Search Report and Written Opinion for PCT/US12/32355 dated Aug. 3, 2012.

Information Disclosure Statement submitted for U.S. Appl. No. 12/502,038, Dec. 30, 2009.

* cited by examiner

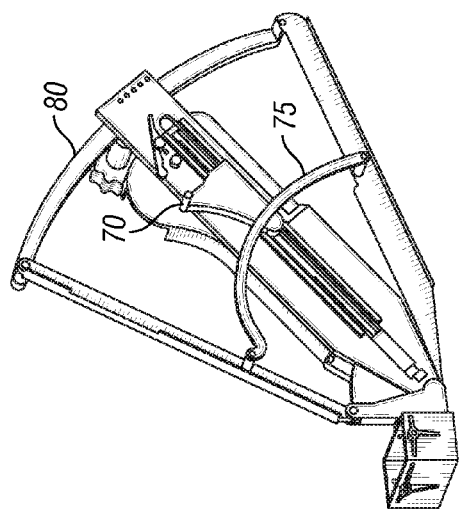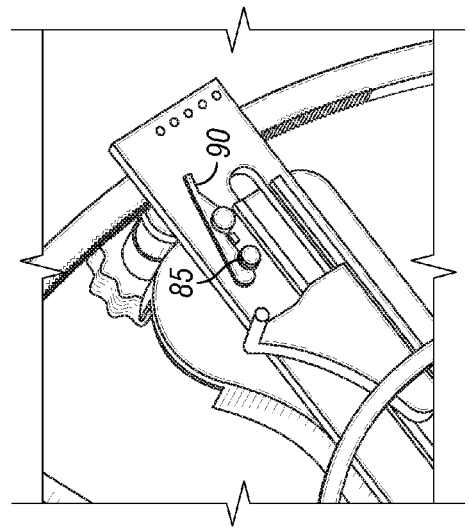
FIG. 2A  FIG. 2B
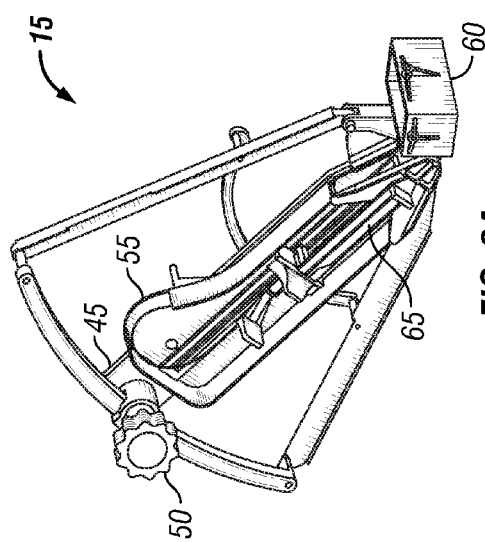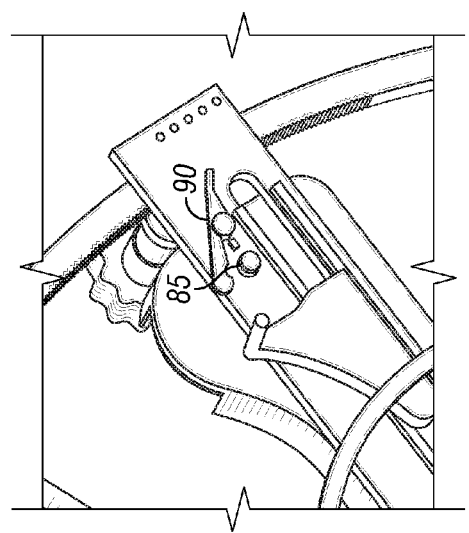
FIG. 3A  FIG. 3B

SYSTEMS AND METHODS FOR ACCESSING THE LUMEN OF A VESSEL

STATEMENT REGARDING FEDERALLY SPONSORED RESEARCH

Not Applicable

RELATED APPLICATIONS

Not Applicable

FIELD OF THE INVENTION

This invention relates to imaging assisted access of the lumen of vessels. More particularly, systems and methods discussed herein are related to the placement of a sheath, needle, and/or guidewire in a vessel.

BACKGROUND

Medical treatment may require the placement of catheters or the like into a person's body. For example, central venous catheters (also referred to herein as "CVC") are placed in a large vein for a variety of medical purposes. A series of manually performed steps to accomplish CVC placement have remained largely unchanged to date. First, a hollow introducer needle is manually inserted through the skin and placed in the vein. Second, a guide wire is manually inserted through the hollow of the needle into the lumen of the vein. The guide wire is inserted until a portion of the guide wire extends past the end of the needle. In this position, the distal end of the wire is in the central vein and the proximal end is outside the patient's body. The introducer needle, which at this point has the guide wire running through its length, is then removed from the patient by pulling the needle out and over the wire. During removal of the needle, the distal end of the guide wire is undisturbed inside the lumen of the vein. Third, the hollow CVC is placed over the proximal end of the guide wire, and the CVC advanced along the wire, through the skin, the subcutaneous tissues, and into the vein. At its final position, the catheter will have one end in the vein and the other end outside of the body. The guide wire can now be retrieved by pulling the guide wire through the catheter and out of the body, without disturbing the position of the catheter. The catheter can now be used to access to the central venous circulation. This process relies on the medical practitioner to locate the vein and may require several attempts before the CVC is properly placed. Similarly, other medical procedures may require placement of a sheath, needle, and/or guidewire into the lumen of a vessel. Medical practitioners may encounter similar problems when attempting to place a sheath, needle, and/or guidewire into the lumen of a vessel.

More recently, ultrasound has been used to assist in the placement of a CVC in a vein. Ultrasound can be used to locate the venous lumen and provide a visual target. The CVC may be placed manually or a robotic device may be used to place the CVC. Even with ultrasound guidance, a medical practitioner may fail to properly place the CVC. Further, current robotic devices are significantly large, cumbersome, and costly and their use in the placement of CVC is impractical.

SUMMARY

In an illustrative implementation, an apparatus for accessing the lumen of a vessel is provided. The apparatus includes a reusable handheld device and a disposable cartridge. The reusable handheld device includes a imaging device attachment utilized to secure an image capturing instrument, an arm coupled to the imaging device attachment, and a depth scale coupled to the arm, wherein the depth scale provides a scale indicating an insertion depth. The disposable cartridge attaches to the reusable handheld device. The disposable cartridge includes a sheath, needle or guidewire coupled to the disposable cartridge. The sheath or needle extends to the insertion depth when fully advanced, thereby allowing the sheath, needle, or guidewire to access the lumen of a vessel.

In an illustrative implementation, a method for accessing the lumen of a vessel includes the steps of attaching an image capturing instrument to an imaging device attachment of a reusable handheld device, and attaching a disposable cartridge to a reusable handheld device. The reusable handheld device includes the imaging device attachment for securing an image capturing instrument to the reusable handheld device, an arm coupled to the imaging device attachment, wherein the arm provides a cartridge attachment, and a depth scale coupled to the articulating arm, wherein the depth scale provides a scale indicating an insertion depth of the sheath. The method further includes the steps of placing the reusable handheld device on a desired vessel location, determining a depth of the vessel with an imaging device, and adjusting the insertion depth to the depth determined utilizing the depth scale on the reusable handheld device. The method also includes the steps of advancing a first slider in the disposable cartridge a predetermined distance, wherein the first slider advances a needle or sheath to the depth determined with the imaging device.

In an illustrative implementation, an apparatus for accessing the lumen of a vessel includes a reusable handheld device that provides a body providing an image device attachment and an articulating arm and a depth scale coupled to the arm, wherein the depth scale provides a scale indicating an insertion depth. The apparatus also includes a disposable cartridge attached to the reusable handheld device. The disposable cartridge includes a sheath slidably coupled to the disposable cartridge, a needle slidably coupled to the disposable cartridge, wherein the needle extends to the insertion depth when fully advanced, and a guidewire coupled to the disposable cartridge, wherein the guidewire passes through the center of the needle and the sheath.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 2A and 2B are illustrative implementations of a reusable handheld device with disposable cartridge;

FIGS. 3A and 3B are illustrative implementations of a reusable handheld device with disposable cartridge;

DETAILED DESCRIPTION

Figure 1:
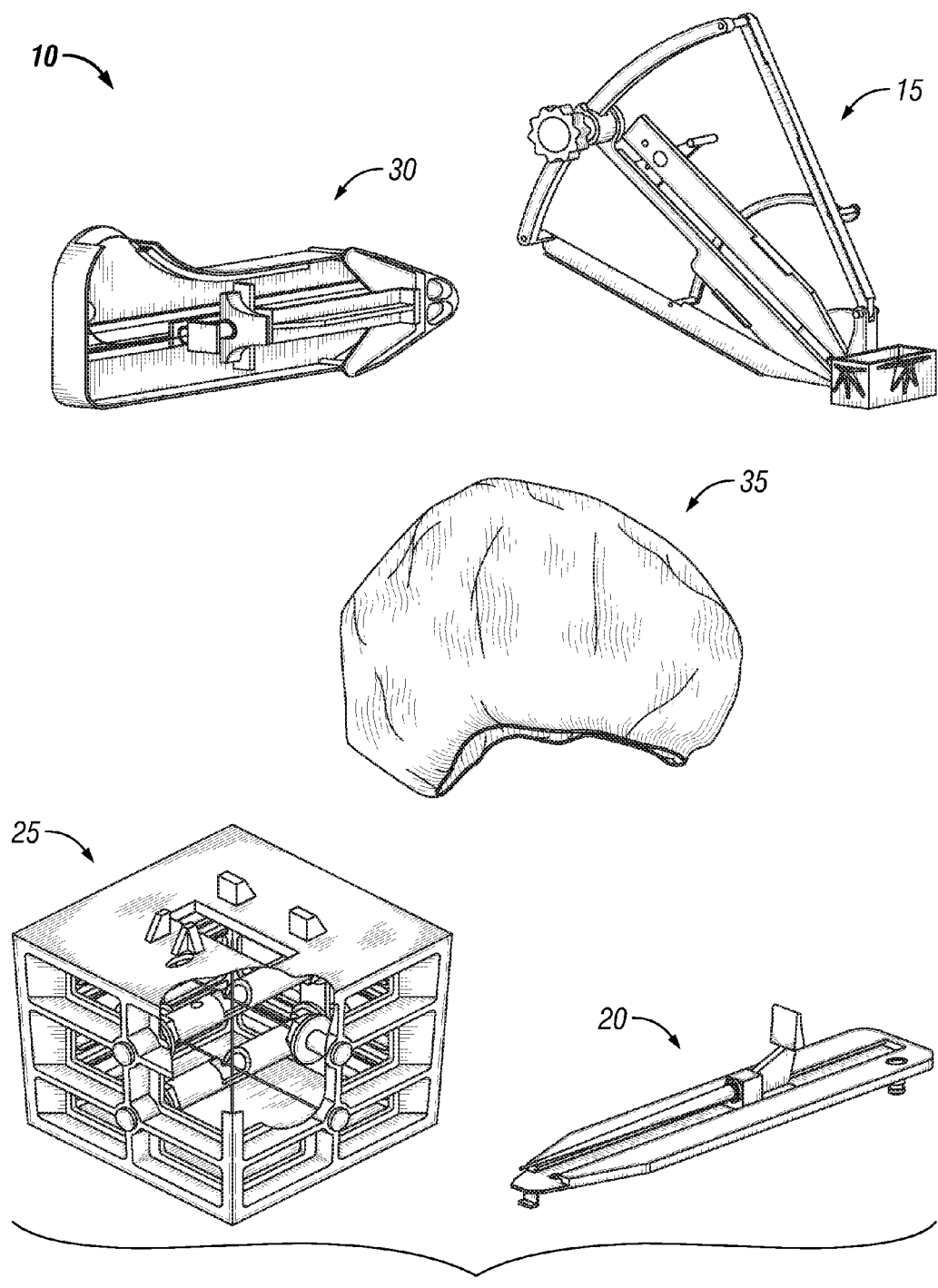
FIG. 1 is an illustrative implementation of an insertion system.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The systems and methods discussed herein are designed to integrate with a commercially available imaging system (e.g. ultrasound system) to provide a medical practitioner with the capability to accurately and reliably accessing the lumen of a vessel located at a depth of 5 mm to 60 mm below the skin surface. For example, the systems and methods discussed herein may be utilized to place a central venous catheter (CVC). While the implementations discussed herein may discuss usage of the systems and methods for starting a CVC, it will be recognized by one of ordinary skill in the art that the scope of the invention is in no way limited to starting a CVC. For example, in other implementations, the system may be utilized to place needle in a vessel; to place a guidewire via a needle placed in a vessel; or to place a sheath via a guidewire that is placed in a vessel via a needle. The systems and methods discussed herein may be utilized in a variety of medical procedures, including, but not limited to: CVC placement, peripherally inserted central catheters, phlebotomy, dialysis access, cardiac catheterization, amniocentesis, cholecystotomy, thoracentesis, paracentesis, and tracheostomy. The insertion system is portable and completely hand operated, requiring no internal or external electrical power source.

FIG. 1 is an illustrative implementation of an insertion system 10. Insertion system 10 may include a reusable handheld device 15, alignment cartridge 20, alignment cube 25, sterile disposable cartridge 30, and cover 35. Reusable handheld device 15 provides for proper alignment of the sheath, needle, and/or guidewire to be inserted into a vessel. Alignment cartridge 20 can be coupled to reusable handheld device 15 and is utilized to perform a check on the alignment of handheld device 15. Alignment cube 25 is utilized to properly align an imaging system (not shown) coupled to reusable handheld device 15. Disposable cartridge 30 can be coupled to reusable handheld device 15 and may include a needle, guidewire, dilator, sheath, and other components utilized to place a CVC or the like. Sterile cover 35 may be place on reusable handheld device 15 to prevent contamination or the like. Sterile cover 35 may be placed on or around reusable handheld device 15 and disposed of after usage.

FIGS. 2A and 2B are illustrative implementations of a reusable handheld device 15. For the purposes of illustration and clarity, reusable handheld device 15 is shown without an imaging device and sterile cover. An imaging device, such as an ultrasound, can be coupled to reusable handheld device 15, but the imaging device is not a part of the reusable handheld device and may be removed when desired. This arrangement allows any suitable brand or type of imaging device to be utilized with handheld device 15.

Reusable handheld device 15 may include an articulating arm 45, thumb wheel 50, cartridge 55, imaging device attachment 60, removable lock bar, 65, slider stop bar 70, slide stop 75, and depth adjustment scale 80. Imaging device attachment 60 is utilized to secure the image capturing instrument of an imaging device to reusable handheld device 15. For example, an ultrasound transducer may be placed in imaging device attachment 60 and secured to reusable handheld device 15. Reusable handheld device 15 may provide attachment points to hold and support cartridge 55 on articulating arm 45. For example, cartridge 55 may be an alignment cartridge or disposable cartridge. Reusable handheld device 15 also includes a thumb wheel 50 that changes the angle of articulating arm 45.

Removable lock bar 65 locks sliding mechanisms on cartridge 55 in place and may be place onto cartridge 55 to prevent inadvertent advancement or insertion of a needle, catheter, and/or the like. Slider stop bar 70 on cartridge 55 slides in the direction of slide stop 75 when a needle slider or needle is advanced. Slider stop bar 70 impedes advancement of the needle when it comes into contact with slide stop 75, thereby preventing a medical practitioner from over advancing a needle past a target vessel. Reusable handheld device 15 may also include a depth adjustment scale 80. When a desired depth is determined using an imaging device, thumb wheel 50 and depth adjustment scale 80 may be utilized to adjust articulating arm 45 to the correct angle for reaching the desired depth.

FIGS. 3A and 3B are illustrative implementations of a reusable handheld device 15 and cartridge 55. When cartridge 55 is mated correctly to reusable handheld device 15, locking pin 85 protruding from the bottom of cartridge 55 extends through articulating arm 45 of reusable handheld device 15. Articulating arm 45 provides locking arm 90 for securing cartridge 55 to reusable handheld device 15. For example, locking pin 85 may provide a groove that locking arm 90 may be place into for securing cartridge 55. While locking pin 85 and locking arm 90 are provided in the figure shown, it should be recognized by one of ordinary skill in the art that any suitable securing means may be substituted.

Figure 4A:
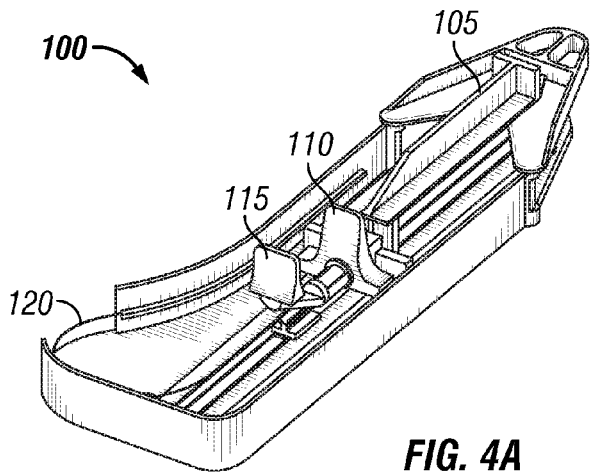
FIGS. 4A and 4B are illustrative implementations of a disposable cartridge.
Figure 4B:
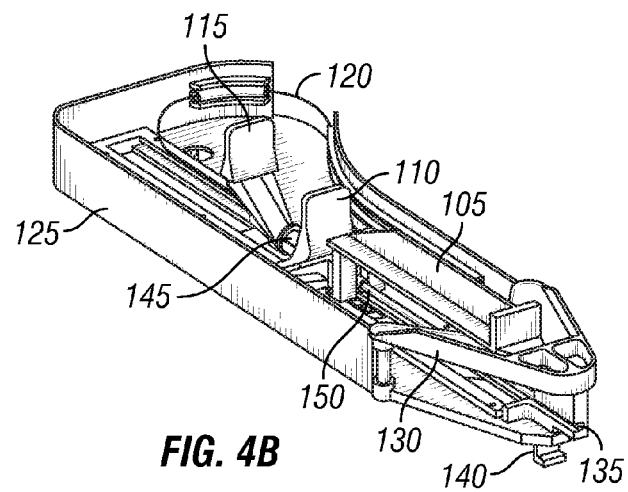

FIGS. 4A and 4B are illustrative implementations of a disposable cartridge 100. Disposable cartridge 100 is sterile to prevent the spread of bacteria, disease, etc. Disposable cartridge 100 will be disposed after a single use. Disposable cartridge 100 may include lock bar 105, sheath slider 110, needle slider 115, guidewire 120, cartridge base 125, span brace 130, guide slot 135, and attachment tab 140. Attachment tab 140 is an L-shaped tab that may be secured to the reusable handheld device. A locking pin and attachment tab 140 mate disposable cartridge 100 to the reusable handheld device.

Lock bar 105 is designed to secure the sheath slider 110, needle slider 115, and/or associated medical components in a desired position to prevent undesired movement before lock bar 105 is removed. For example, during shipping, before attachment to the reusable handheld device, and/or prior to use it is desirable to prevent a sharp needle and sheath from protruding from disposable cartridge 100. However, when disposable cartridge 100 is attached to a reusable handheld device that is ready for use, lock bar 105 may be removed to allow sheath slider 110, needle slider 115, and associated medical components to be freely advanced and retracted.

Disposable cartridge 100 may also include a sterile needle 145, sheath 150, and guidewire 120. Guidewire 120 runs inside a track located in the wall of disposable cartridge 100 and continues through the inside of needle 145. Needle 145 is positioned in the center of sheath 150 and may slide into and out of sheath 150. In some implementations, a dilator may be provide in between needle 145 and sheath 150 to minimize or prevent bending of needle 145. There are two sliders in disposable cartridge 100. Needle slider 115 controls the advancement and retraction of the needle 145. Needle slider 115 is coupled to slider stop bar 70 shown in FIG. 2B. As needle slider 115 is advanced, slider stop bar 70 is also advanced. The depth the tip of needle 145 extends from reusable handheld device 15 is determined by rotating thumb wheel 50 until depth adjustment scale 80 on reusable handheld device 15 shows the desired depth. Pushing needle slider 115, toward a patient until the slider stop bar 70 hits slide stop 75, causes needle 145 to extend out from disposable cartridge 100 and into a patient to the desired depth. Moving needle slider 115 away from the patient until it hits the proximal end of a slider track fully retracts needle 145 into disposable cartridge 100.

Sheath slider 110 controls the advancement and retraction of sheath 150. Because sheath slider 110 is placed in front of needle slider 115, advancing needle slider 115 also causes sheath slider 110 to advance. However, retracting of needle slider 115 does not cause sheath slider 110 to retract. Additionally, sheath slider 110 is not coupled to slider stop bar 70, which allows sheath slider 110 to be advanced further than needle slider 115. Sheath 150 has a larger diameter than needle 145 and is placed over the needle. Guidewire 120 passes through needle 145. Pushing sheath slider 110 toward the patient advances sheath 150 over needle 145 tracking over guidewire 120 and into a target vessel. Guide slot 135 supports needle 145 during insertion. Guide slot 135 does not completely surround needle 145 or sheath 150 so as to provide an exit point for the sheath 150 after it has been inserted into the patient. Disposable cartridge 100 may provide an opening below span brace 130 that allows sheath 150 to be easily removal of from disposable cartridge 100.

Figure 5:
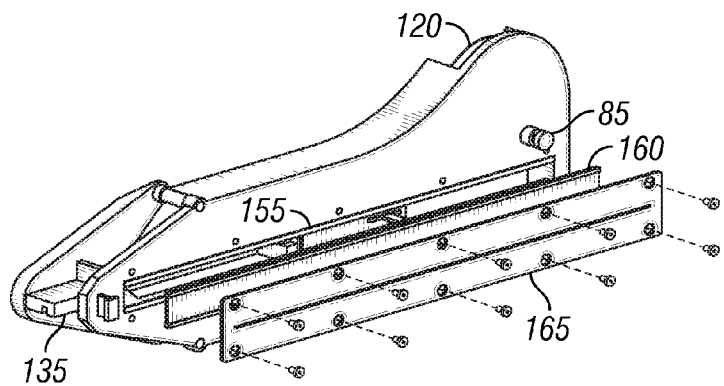
FIG. 5 is an illustrative implementation of a back portion of a disposable cartridge.

FIG. 5 is an illustrative implementation of a back portion of a disposable cartridge 100. Both the needle and sheath sliders run along slider track 155. A seal 160 may be place on slider track 155 to maintain a seal around a slider as it moves along slider track 155. Slider track plate 165 is place over seal 160 and may be secured to disposable cartridge 100. Disposable cartridge 100 may also include a sterile cover attached to the cartridge via slider track plate 165 or any other suitable attachment point. The cover can be positioned over an image capturing instrument and the reusable handheld device when disposable cartridge 100 is attached to the reusable handheld device 15. This sterile cover is not shown in the figures above to provide an unobstructed view of the disposable cartridge features. Guidewire 120 is advanced by grasping the guidewire with the forefinger and thumb and moving it in a proximal direction. This will cause guidewire 120 to advance in the distal direction through the needle into the patient's vessel. During advancement of guidewire 120, the operator may view the advancement of guidewire 120 on a display of the imaging device. Guidewire 120 may also be advanced by grasping the guidewire proximal to the needle hub and moving the guidewire through the needle into the patient's vessel.

Figure 6:
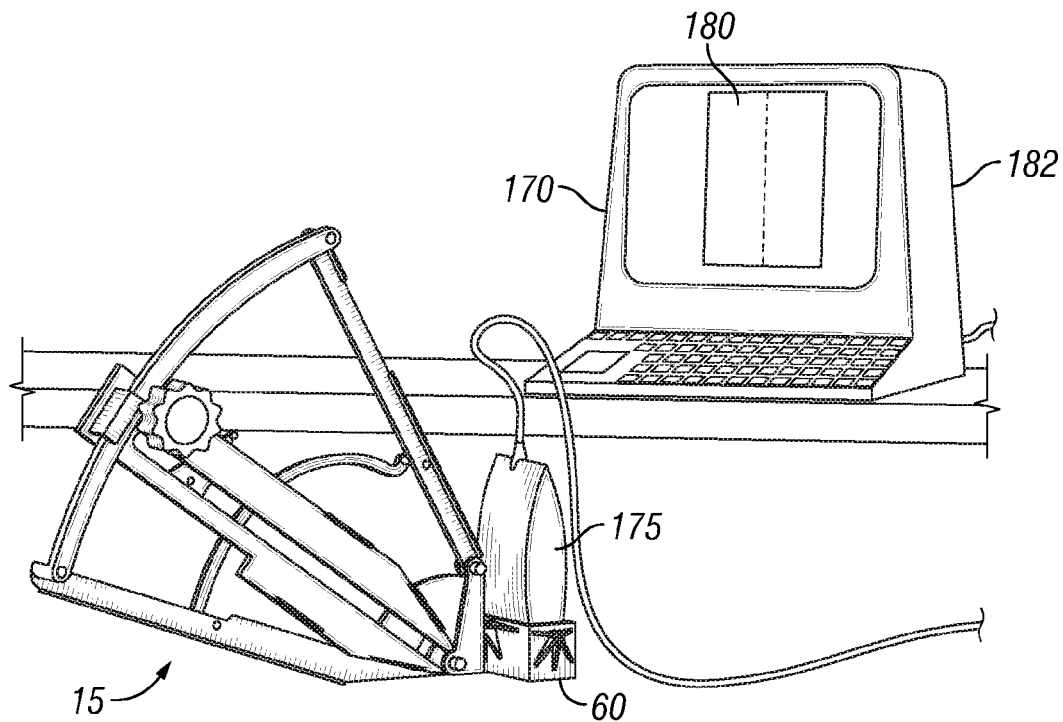
FIG. 6 is an illustrative implementation of a reusable handheld device and imaging device.

FIG. 6 is an illustrative implementation of a reusable handheld device 15 and imaging device 170. Imaging device 170 may include an image capturing instrument 175 that may be secured in imaging device attachment 60 of reusable handheld device 15. Image capturing instrument 175 may send and/or received signals utilized to generate images. Imaging device 170 receives data from image capturing instrument 175 and shows the generated images on display 182. For example, a commercially available ultrasound imaging device may be utilized and the ultrasound transducer may be secured in imaging device attachment 60 of the reusable handheld device 15. Screen overlay 180 is a transparent adhesive film that may include a vertical dashed line in the center and tick marks on each side. Screen overlay 180 is designed to fit on and adhere to a display 182 of imaging device 170. Screen overlay 180 provides an operational reference for use of insertion system 10.

Figure 7:
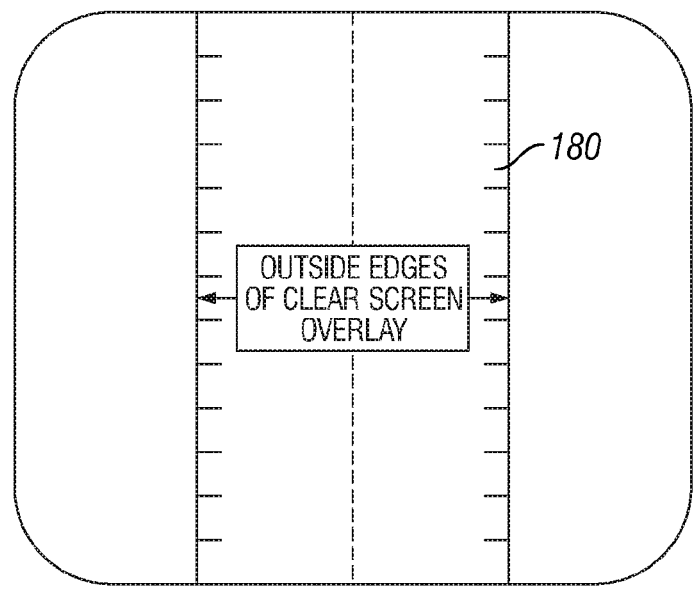
FIG. 7 is an illustrative implementation of a screen overlay.

FIG. 7 is an illustrative implementation of a screen overlay 180. Screen overlay 180 may be a clear, thin, plastic sheet with low tack adhesive that can be affixed to a display 182 of imaging device 170. Screen overlay 180 may provide a vertical dashed center line and tick marks on each side that provides a visual reference aid to the user. Screen overlay 180 and imaging device 170 allow the medical practitioner to accurately locate a vessel and determine the depth of the vessel. The medical practitioner may then set insertion system 10 to the measured depth via hand control of thumb wheel 50 and insert the needle 145, sheath 150, and/or guidewire 120 via hand control of the needle slider 115, sheath slider 110, and/or guidewire 120. It should be noted that an image capturing instrument 175 of the imaging device 170 connects to the reusable handheld device, but imaging device 170 is not part of the insertion system. Since medical facilities may already have a suitable imaging device, utilizing an existing imaging device, rather than incorporating the imaging device, reduces cost. This also allows the sheath insertion methods and systems discussed herein to easily be adapted for use with a variety of different types and/or brands of imaging devices. Imaging devices that are suitable for use with the insertion systems discussed herein will preferably be capable of imaging and measuring depths of approximately 5 mm to 60 mm.

Figure 8:
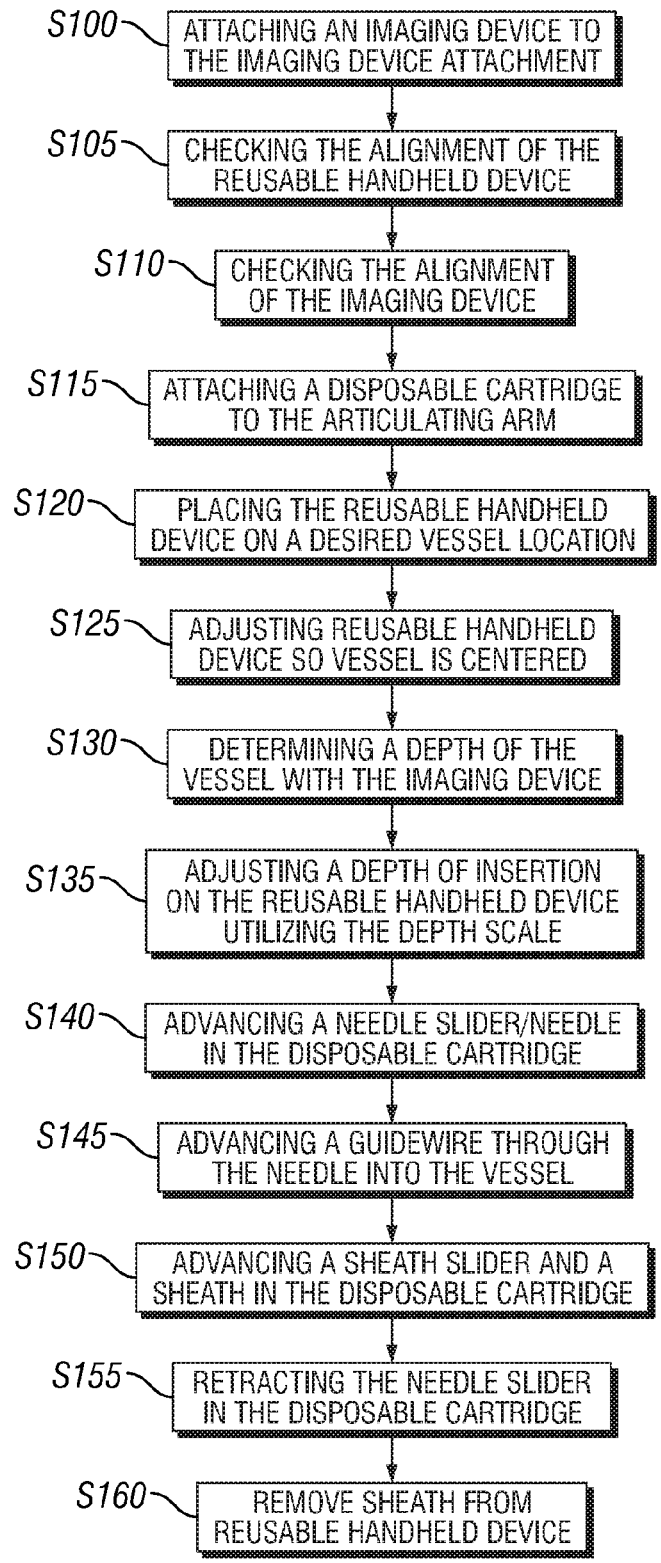
FIG. 8 is an illustrative implementation of a method for inserting a sheath into a vessel.

FIG. 8 is an illustrative implementation of a method for inserting a sheath into a vessel. While the following provides a description of inserting a sheath into a vessel, it will be recognized by one of ordinary skill in the art that the device is suitable for a variety of medical procedures involving the insertion of a sheath, needle, and/or guidewire into the lumen of a vessel. The scope of the claims is in no way limited to inserting a sheath into a vessel, except where expressly stated in the claims. For example, in other implementations, the insertion system may simply be utilized to place a needle in the lumen of a vessel or to place a guidewire in the lumen of a vessel with the aid of a needle. To prepare insertion system 10 for use, the user will integrate the reusable handheld device 15 with imaging device 170 in step S100 by placing image capturing instrument 175 in imaging device attachment 60 and securing it with the thumb screws or the like. In step S105 the alignment of the reusable handheld device 15 may be checked with an alignment cartridge 20. In step S110 the alignment of the imaging device 170 can be check with an alignment cube 25. During this alignment, screen overlay 180 may be placed on the display of the imaging device 170. Aligning the reusable handheld device 15 and imaging device 170 with an alignment cartridge 20 and alignment cube 25 are discussed in further detail below. Note that the alignment steps S105 and S110 are optional steps that are performed for best results. However, in the case that alignment checks have been previously performed in the same day or recently, it may not be necessary to perform the alignment checks. Additionally, many of the steps for the method discussed herein may be performed in a different sequence than shown or omitted. The scope of methods for inserting a sheath into a vessel is in no way limited to the particular methods illustrated herein. One of ordinary skill in the art will recognize a variety of potential variations in the sequence and particular steps performed.

Disposable cartridge 100 can be attached to the articulating arm 45 of reusable handheld device 15 in step S115. Next, reusable handheld device 15 can be placed on a desired vessel location to find a target vessel in step S120. The display of the imaging device will provide an image of desired location. In step S125, the operator may adjust reusable handheld device so the target vessel is centered on the vertical dotted line of screen overlay 180. The operator may then utilize the imaging device 170 to determine the target depth of the vessel in step S130. The target depth indicates the distance from the top surface (or skin of the patient) to the center of the vessel. When the target depth of the vessel is determined, the operator can adjust the thumb wheel 50 to modify the insertion depth of the needle utilizing the depth adjustment scale 80 on reusable handheld device 15 in step S135. Once the operator has modified the insertion depth to the target depth, the needle slider 115 can be advanced to insert the needle 145 into the patient in step S140.

Once the needle 145 is fully advanced, the operator can advance the guidewire 120 through the needle into the target vessel in step S145. Next, sheath slider 110 can be advanced to move sheath 150 along guidewire 120 into the target vessel in step S150. Now that the sheath 150 is in the target vessel, the needle slider can be retracted in step S150. Finally, in step S160, sheath 150 can be removed from reusable handheld device 15, thereby completing placement of the sheath in the target vessel.

Two alignment tasks may be performed to check the alignment of the reusable handheld device 15. The first step in the alignment process is performed as part of the preparation procedure to ensure correct positioning of the image capturing instrument 175 in the imaging device attachment 60. The second step in the alignment check is performed to confirm that the slide stop 75 on the reusable handheld device 15 is in the correct position. Both alignment tasks can be performed in a non-sterile or sterile environment.

Figure 9:
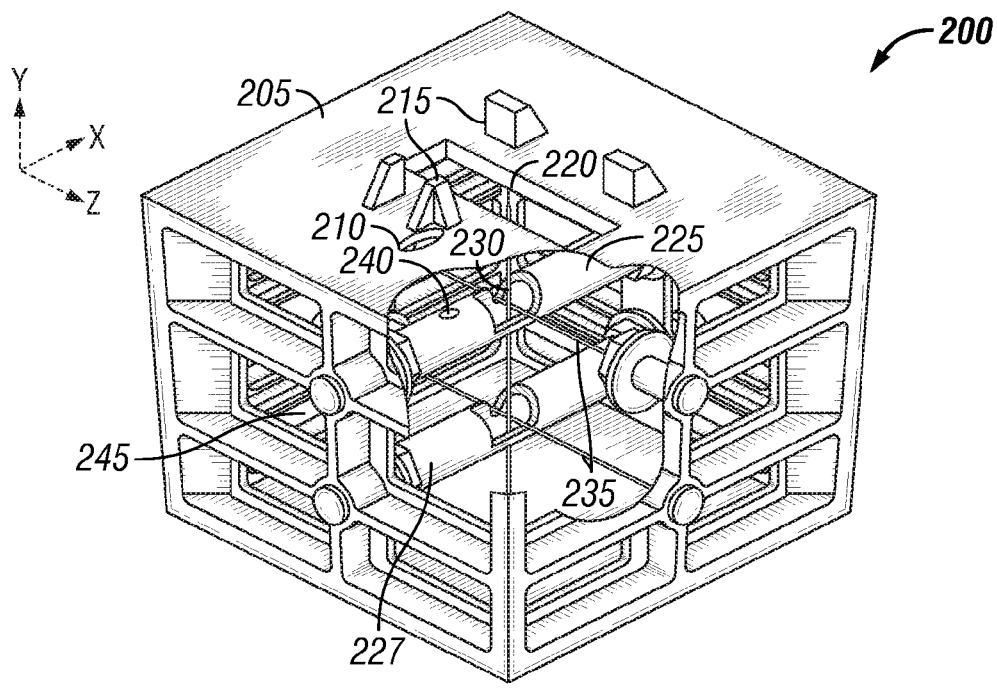
FIG. 9 is an illustrative implementation of an alignment cube.

FIG. 9 is an illustrative implementation of an alignment cube 200. Alignment cube 200 enables the user to perform alignment tasks. Top lid 205 of alignment cube 200 provides a needle insertion port 210, alignment guides 215, and image capturing window 220. Needle insertion port 210 provides an entry point for the stylet 320 to enter alignment cube 200. Alignment guides 215 receive the imaging device attachment 60 of the reusable handheld device 15 and serve to properly align the reusable handheld device 15 to alignment cube 200. Image capturing window 220 provides an opening for the image capturing instrument 175 of the imaging device. Image capturing window 220 is directly above the shallow vessel target (X-Axis) 225 and deep vessel target (X-Axis) 227 in alignment cube 200.

The shallow vessel target 225 is positioned at a depth of 30 mm and the deep vessel target 227 is positioned at a depth of 60 mm. The shallow vessel target 225 and deep vessel target 227 are arranged perpendicular to the image capturing window 220 and horizontal to the top lid 205, defining the x-axis of the alignment cube 200. Both the shallow vessel target 225 and deep vessel target 227 in the alignment cube 200 includes a premeasured and marked target center point. In particular, the target center points are indicated by wire structures intersecting shallow vessel target 225 and deep vessel target 227. Target wire (Y Axis) 230 is arranged vertically or along the y-axis in alignment cube 200. Two target wires (Z-Axis) 235 are arranged perpendicular to the shallow vessel target 225 and deep vessel target 227 along the z-axis in alignment cube 200. Target wire (Z-Axis) 235 are perpendicular to shallow vessel target 225, deep vessel target 227 and target wire (Y-Axis) 230. The shallow vessel target 225 at a depth of 30 mm may include a stylet window 240 that allows the stylet to pass through to the deep target vessel 227. This stylet window 240 allows the needle/stylet to reach deep vessel target 227 at a depth of 60 mm. Alignment cube 200 may include several viewing windows 245, or the sides of the cube may be made of a transparent material, to allow a user to view the alignment process of the reusable handheld device 15. Alignment cube 200 and the shallow vessel target 225 and deep vessel target 227 can be filled with water by the user to accommodate the imaging signal.

Figure 10:
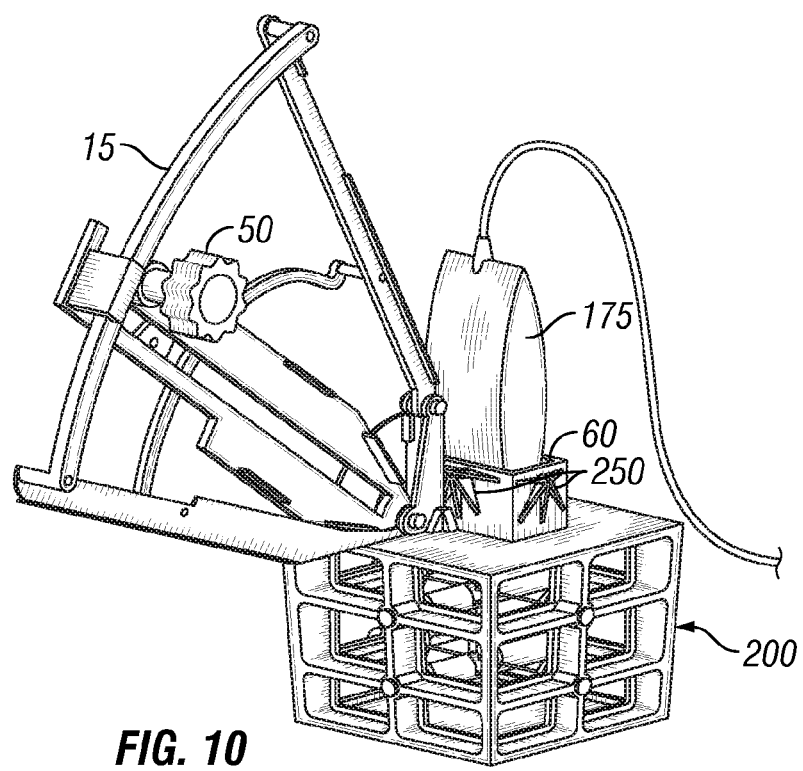
FIG. 10 is an illustrative implementation of a reusable handheld device and image capture instrument placed on top of an alignment cube.

FIG. 10 is an illustrative implementation of a reusable handheld device 15 placed on top of an alignment cube 200. The first step in the alignment process is to attach the image capturing instrument 175 to the reusable handheld device 15 and secure it in place with the thumbscrews 250. Note that image capturing instrument 175 and reusable handheld device 15 should be cleaned and disinfected prior to the first alignment check. With the image capturing instrument 175 attached, the user can power on the imaging device. After filling the alignment cube 200 with water, the reusable handheld device 15 may be placed on top of the alignment cube 200. Image capturing instrument 175 is repositioned in the imaging device attachment 60 to make sure that it is positioned correctly and properly aligned.

Figure 11:
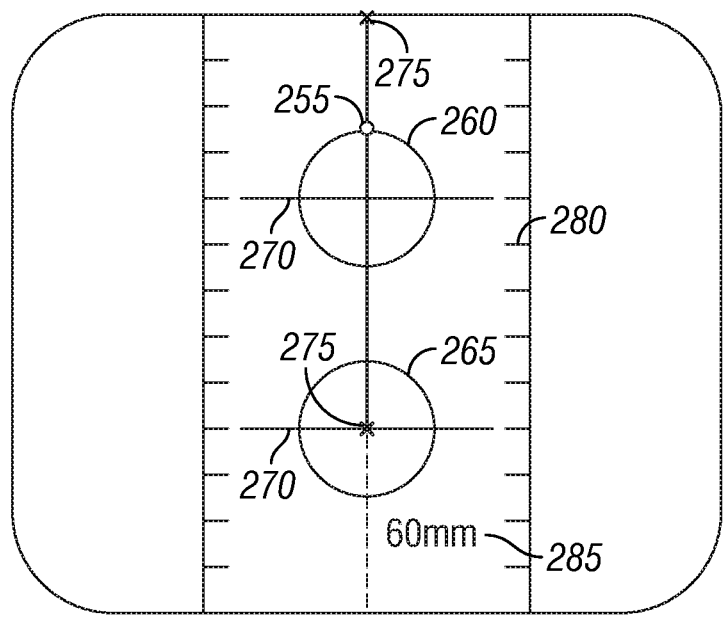
FIG. 11 is an illustrative implementation of a image displayed on an imaging device when a reusable handheld device is placed on top of an alignment cube.

In order to properly align image capturing instrument 175, target vessels 225, 227 and target wires 230, 235 should be properly aligned on the display of the imaging device. Once target vessels 225, 227 and target wires 230, 235 are properly aligned on the display, screen overlay 180 should be positioned in alignment with target vessels 225, 227 and target wires 230, 235 displayed on imaging device 170. For example, screen overlay 180 may be position as shown in FIG. 11. When image capturing instrument 175 and screen overlay 180 are properly aligned, the vertical dashed centerline of screen overlay 180 corresponds to a plane of the needle and sheath.

FIG. 11 is an illustrative implementation of a image displayed on an imaging device when a reusable handheld device 15 is placed on top of an alignment cube 200. When image capturing instrument 175 is properly aligned, the image resulting from placing reusable handheld device 15 on top of an alignment cube 200 should resemble FIG. 11. The ultrasound system display should show two circles 260, 265 aligned vertically in the center of the screen representing the shallow target vessel 225 and deep target vessel 227 at 30 mm and 60 mm, respectively, in alignment cube 200. Each of the circles 260, 265 will have a bright horizontal line 270 through the center. Vessel targets 225, 227 have target wires 235 travelling along the z-axis of alignment cube 200 passing through them. Target wires 235 are represented by horizontal lines 270 passing though the top circle 260 and bottom circle 265. During the alignment check, the user can rotate the image capturing instrument 175 about the x-axis until horizontal lines 270 in the 30 mm and 60 mm vessel simulation are horizontal. Horizontal tick marks 280 may be provided by screen overlay 180 to help the operator determine a horizontal position. The user may then pitch the image capturing instrument 175 about the z-axis until the circles 260, 265 are clear and a small white circle 255 representing target wire 230 appears at the top center of the 30 mm vessel simulation image circle 260.

Holding that position, the user or an assistant can hand tighten thumb screws 250 on the imaging device attachment 60. Screen overlay 180 should be placed on the screen so that the center line dissects circles 260,265 through small white circle 255 at the top center and horizontal lines 270 looks horizontal when compared to the side tick marks. The final check of the alignment process is to use the depth measuring capability of the ultrasound system to measure the depth of the Z-axis vessel simulation wire at 60 mm. This is done by placing a mark 275 on the top of the display and another mark 275 (vertically aligned) on the image of the Z-axis of the 60 mm vessel simulation. Measured distance 285 computed by the imaging device should match the known depth of the wire i.e. 60 mm. Similarly, a check may be performed on the vessel target at 30 mm.

Figure 12:
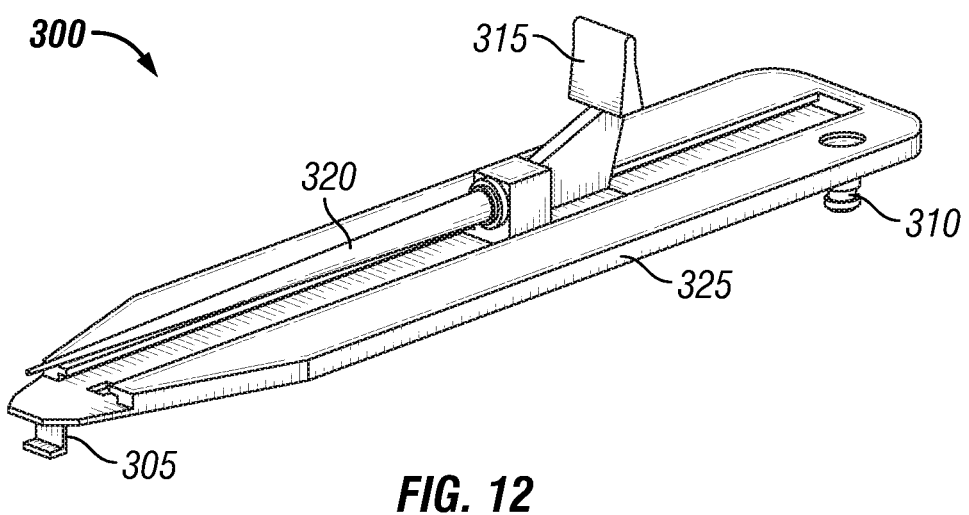
FIG. 12 is an illustrative implementation of an alignment cartridge.

The purpose of the second alignment check procedure is to ensure that the mechanical structure and sliders have not moved out of position due to misuse or damage. FIG. 12 an illustrative implementation of an alignment cartridge 300. Alignment cartridge 300 can be used to perform the alignment check procedure. Alignment cartridge 300 has the same interfaces and attachment points as the disposable cartridge, but does not contain any medical components. Similar to the disposable cartridge, attachment tab 305 and locking pin 310 are utilized to attach alignment cartridge 300 to the reusable handheld device. Alignment cartridge 300 provides a stylet slider 315 attached to a stylet 320 that is the same length as the needle in the sterile disposable cartridge. Cartridge base 325 provides an opening that receives stylet slider 315 and allows stylet slider 315 to be advanced and retracted.

The user begins the procedure in a non-sterile or sterile environment by placing the image capturing instrument 175 in imaging device attachment 60 and securing it in place with the thumb screws 250. With image capturing instrument 175 securely in place, the user attaches the alignment cartridge 300 to the reusable handheld device 15. After filling the alignment cube 200 with water, the user can follow the previously discussed alignment steps discussed above, if necessary, to align the position of the image capturing instrument if necessary. However, note that a screen overlay is not required to perform the alignment check procedure.

When the image capturing alignment or first alignment check is successfully completed, the user can set the thumb wheel 50 on the reusable handheld device 15 to a depth of 30 mm and actuate stylet slider 315 on alignment cartridge 300. When the slider stop bar 70 hits the slide stop 75, the distal end of stylet 320 should touch the intersection point at 30 mm between z-axis wire 235 and y-axis wire 230. Visual confirmation of this is made by looking through the viewing windows on the sides of the alignment cube. The user can then repeat this procedure for the intersection point at 60 mm between the z-axis wire 235 and y-axis wire 230. If visual confirmation indicates that the stylet does not touch the intersection points of the wires at 30 mm or 60 mm, the reusable handheld device is recalibrated and adjusted for proper alignment.

An example of a method for inserting a sheath into a vessel is discussed in detail below. In particular, the method discussed utilizes an ultrasound imaging device with insertion system 10. Initially, first and second alignment checks are performed with alignment cube 200 and alignment cartridge 300 as described previously. With the alignment checks complete, the insertion system is ready for use on the patient. Preparation may include, if necessary, positioning the patient, disinfecting the procedure site, draping the procedure site, administering anesthesia, and the like. The final patient preparation step is the application of sterile ultrasound gel to the procedure site. With patient preparation complete, the user applies the sterile ultrasound gel to the image capturing instrument 175 and attaches the sterile disposable cartridge 100 to reusable handheld device 15. With gel correctly applied to the image capturing instrument 175 and sterile disposable cartridge 100 attached, the user positions sterile cover 35 over reusable handheld device 15 and image capturing instrument 175. With the cover correctly positioned, the user can place reusable handheld device 15 on the patient at the procedure site and begin to receive ultrasound images of the patient's vessel(s) displayed on the display. The ultrasound imaging display, with screen overlay 180, allows the user to adjust reusable handheld device 15 until the desired target vessel is centered on the vertical dotted line on screen overlay 180 or the target plane of needle 145 and sheath 150. The user can use the distance measuring capability of the ultrasound imaging device to measure the depth to the center of the target vessel. Additionally, the user can use the distance measuring capability of the ultrasound imaging device to measure the semi-major axis and semi-minor axis of the vessel image to determine the diameter of the target vessel. The depth of the vessel should be between 5 mm and 60 mm, and the diameter of the vessel should be at least 4 mm in diameter. If the depth or diameter is inappropriate, the user should select a different place along the vessel where the depth and diameter are satisfactory. To set reusable handheld device 15 to the depth value obtained from the depth measurement, the user actuates the thumb wheel 50 to the targeted depth. With depth setting on the reusable handheld device 15 achieved, the user may then actuate needle 145 by moving the needle slider 115 of disposable cartridge 100 toward the patient. This inserts needle/dilator 145 into the patient and places the needle in the center of the target vessel. With needle/dilator 145 fully advanced into the patient's vessel, the user can actuate guidewire 120 by using his/her index finger to press against and advance guidewire 120 toward the patient. Using this motion, the user can advance the guidewire 120, through the proximal end of needle 145 to desired length beyond the distal end of the needle. The user can evaluate the placement of the guidewire via the ultrasound image display 182.

With guidewire 120 fully advanced into the patient's vessel, the user can actuate sheath slider 110 on the disposable cartridge toward the patient until sheath slider 110 reaches the end of slider track 155. The guidewire 120, needle 145, and sheath 150 are now resident in the target vessel. The user can fully retract needle 145 by moving needle slider 115 away from the patient, while maintaining sheath slider 110 and sheath 150 in the fully advanced position. This will retract needle 145 completely back into disposable cartridge 100 and out of sheath 150.

With sheath insertion complete, the user can remove sheath 150 from the guide slot 135. While holding sheath 150 and guidewire 120 in place, the user may remove reusable handheld device 15 from the patient. As reusable handheld device 15 is moved away from the patient, the proximal end of guidewire 120 slides through needle 145 and separates from disposable cartridge 100. Disposable cartridge 100 is then removed from reusable handheld device 15 and disposed. Image capturing instrument 175 and reusable handheld device 15 may then be separated from each other, cleaned, disinfected, and stored.

Figure 13A:
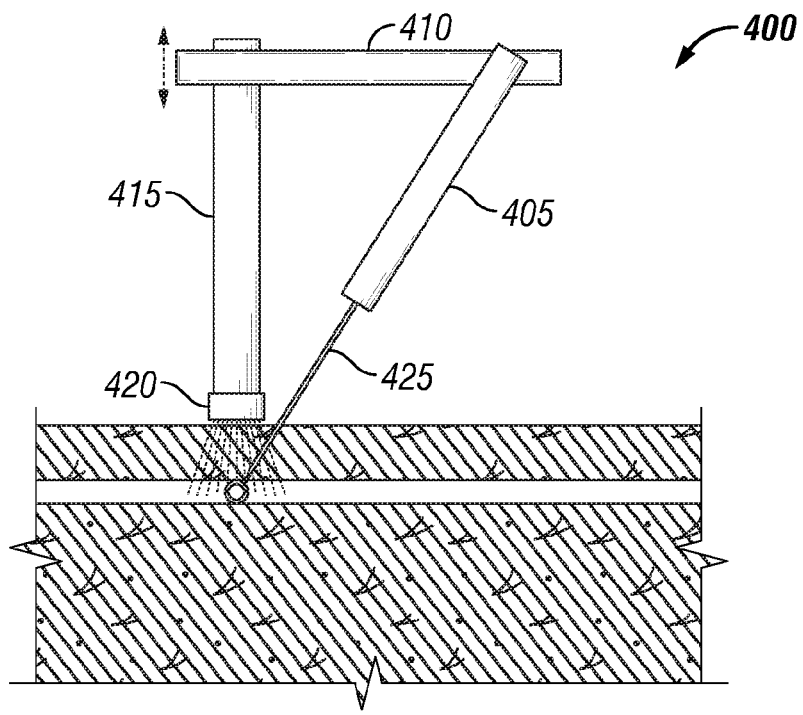
FIGS. 13A and 13B are illustrative implementations of a second arrangement for an insertion system.
Figure 13B:
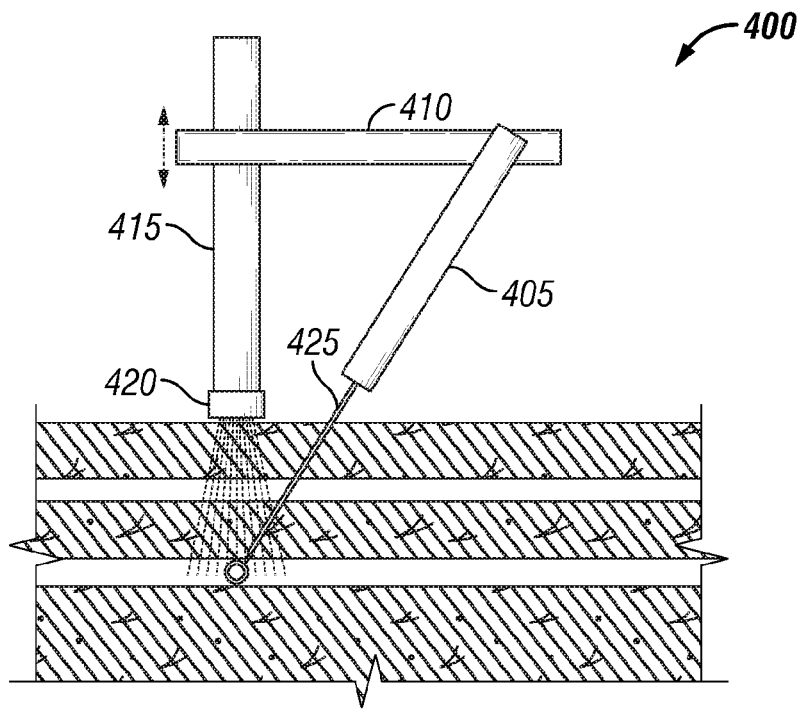

FIGS. 13A and 13B are illustrative implementations of a second arrangement for an insertion system 400. In insertion system 400, cartridge 405 is fixed at a predetermine angle. While cartridge 405 is shown independently attached to boom 410, in other implementations, cartridge 405 may be secured to fixed arm in a similar manner as to the articulating arm 45 shown in FIGS. 3A and 3B. Cartridge 405 may be coupled to adjustable boom 410, which may be adjusted vertically to achieve different target depths. Boom 410 is coupled to transducer arm 415. Transducer arm 415 may provide a depth scale that indicates the needle depths of the range of heights for boom 410. Transducer arm 415 provides an attachment for transducer 420. Needle 425 extends to a fixed predetermined length.

Figure 14A:
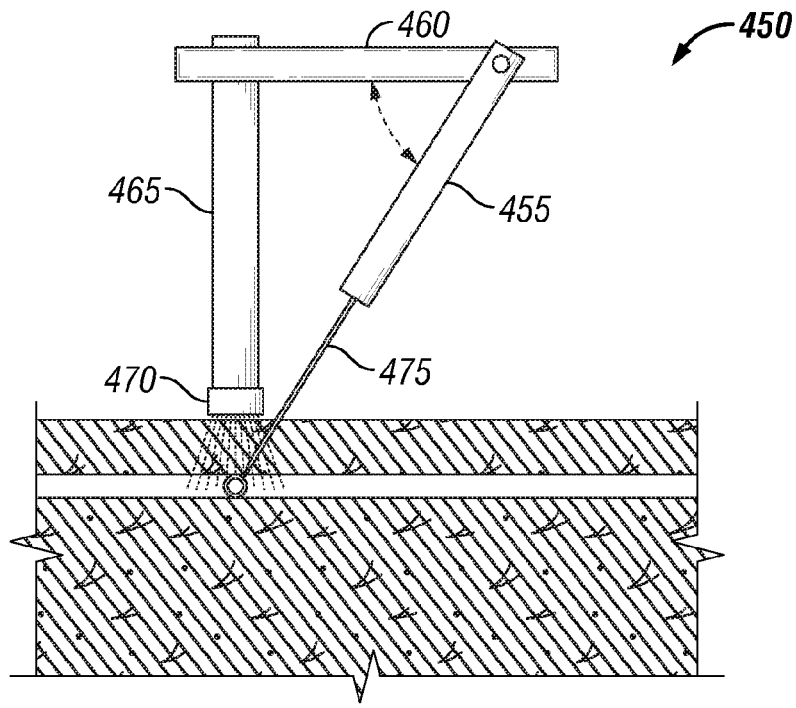
FIGS. 14A and 14B are illustrative implementations of a third arrangement for an insertion system.
Figure 14B:
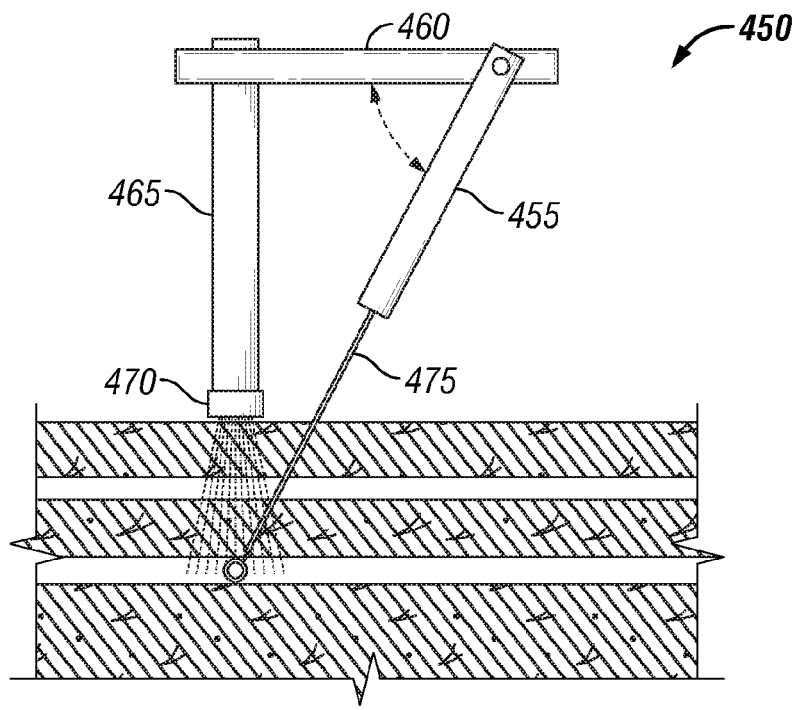

FIGS. 14A and 14B are illustrative implementations of a third arrangement for an insertion system 450. In insertion system 450, cartridge 455 has a variable angle in relation to boom 460. While cartridge 455 is shown independently attached to boom 460, in other implementations, cartridge 455 may be secured to fixed arm in a similar manner as to the articulating arm 45 shown in FIGS. 3A and 3B. In contrast to the previous implementation, boom 460 is a fixed height. Boom 460 is coupled to transducer arm 465, which provides an attachment for transducer 470. Needle 475 is a variable length needle. As the angle of cartridge 455 increase, the depth of insertion increases. The angle of cartridge 455 and length of needle 475 are adjusted to achieve a desired target depth. A depth scale (not shown) for insertion system 450 takes into account the angle of cartridge 455. The depth scale may indicate the depth of needle 475 based on the angle of cartridge 455 and the amount needle 475 has been extended.

Figure 15A:
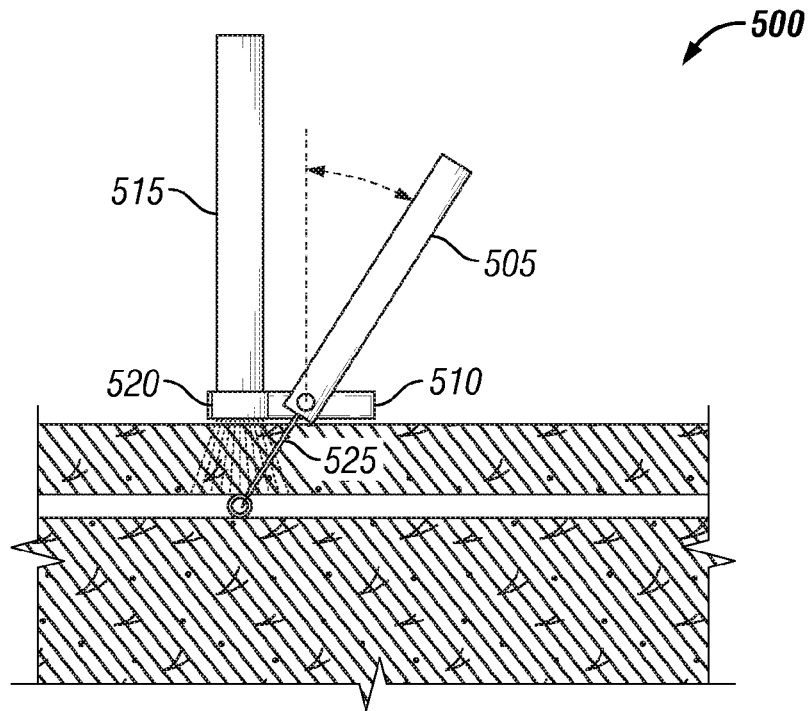
FIGS. 15A and 15B are illustrative implementations of a fourth arrangement for an insertion system.
Figure 15B:
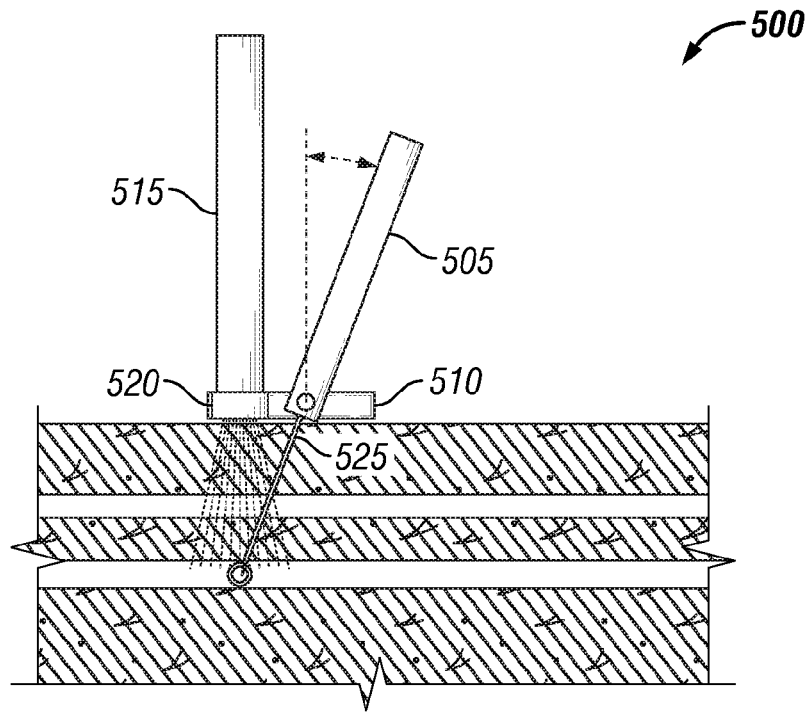

FIGS. 15A and 15B are illustrative implementations of a fourth arrangement for an insertion system 500. In insertion system 500, cartridge 505 has a variable angle in relation to boom 510. While cartridge 505 is shown independently attached to boom 510, in other implementations, cartridge 505 may be secured to fixed arm in a similar manner as to the articulating arm 45 shown in FIGS. 3A and 3B. Boom 510 is fixed near the bottom of transducer arm 515. Transducer arm 515 provides an attachment for transducer 520. Needle 525 is a variable length needle. As in the previous implementation, the angle of cartridge 505 and length of needle 525 are adjusted to achieve a desired target depth. A depth scale (not shown) for insertion system 500 takes into account the angle of cartridge 505. The depth scale may indicate the depth of needle 525 based on the angle of cartridge 505 and the amount needle 525 has been extended.

Figure 16A:
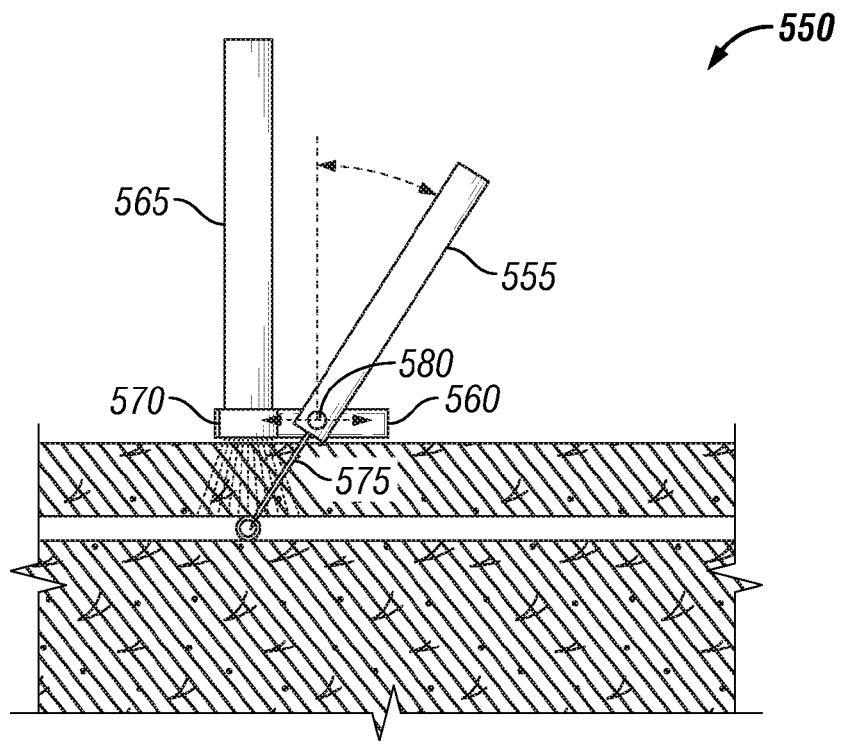
FIGS. 16A and 16B are illustrative implementations of a fifth arrangement for an insertion system.
Figure 16B:
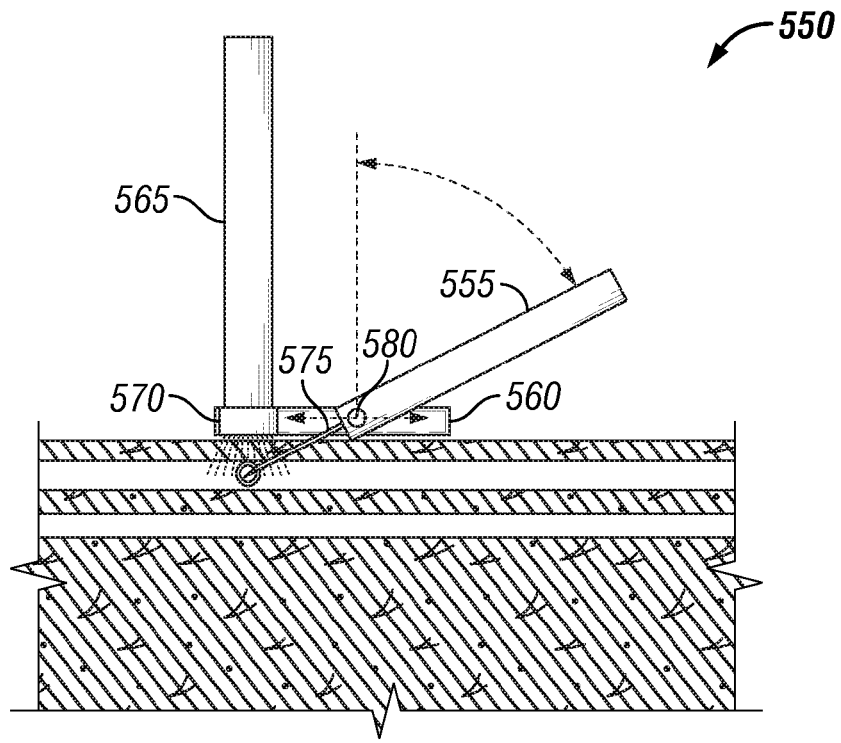

FIGS. 16A and 16B are illustrative implementations of a fifth arrangement for an insertion system 550. In insertion system 550, cartridge 555 has a variable angle in relation to boom 560. While cartridge 555 is shown independently attached to boom 560, in other implementations, cartridge 555 may be secured to fixed arm in a similar manner as to the articulating arm 45 shown in FIGS. 3A and 3B. Boom 560 is fixed near the bottom of transducer arm 565. Transducer arm 565 provides an attachment for transducer 570. Needle 575 is a fixed length needle. In contrast to the previous implementations, cartridge 555 has a variable pivot point 580 that can be moved along boom 560. The angle of cartridge 555 and variable pivot point 580 are adjusted to achieve a desired target depth. A depth scale (not shown) for insertion system 550 takes into account the angle of cartridge 555 and the variable pivot point 580.

Figure 17A:
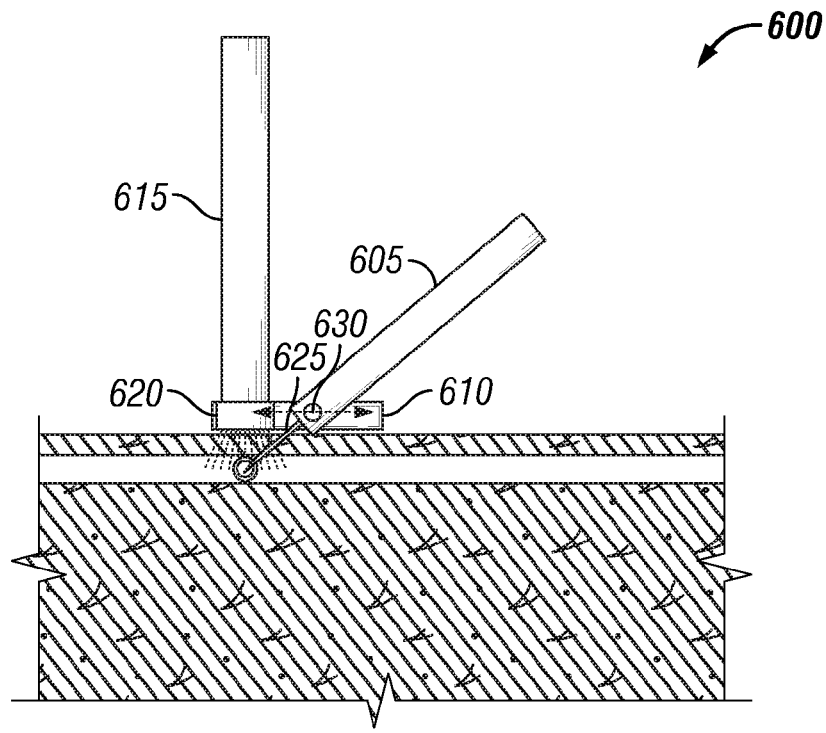
FIGS. 17A and 17B are illustrative implementations of a sixth arrangement for an insertion system.
Figure 17B:
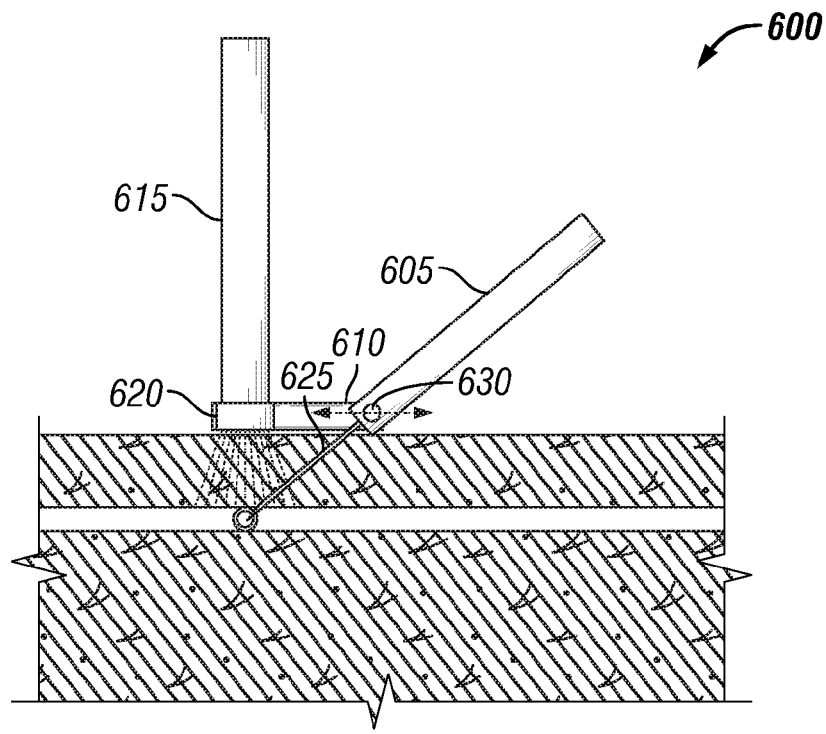

FIGS. 17A and 17B are illustrative implementations of a sixth arrangement for an insertion system 600. In insertion system 600, cartridge 605 has a fixed angle in relation to boom 610. While cartridge 605 is shown independently attached to boom 610, in other implementations, cartridge 605 may be secured to fixed arm in a similar manner as to the articulating arm 45 shown in FIGS. 3A and 3B. Boom 610 is fixed near the bottom of transducer arm 615. Transducer arm 615 provides an attachment for transducer 620. Needle 625 is a variable length needle. Cartridge 605 has a variable pivot point 630 that can be moved along boom 610. The variable pivot point 630 of cartridge 605 and length of needle 625 are adjusted to achieve a desired target depth. A depth scale (not shown) for insertion system 600 takes into account the a variable pivot point 630 and the amount needle 625 has been extended.

From the variety of arrangements discussed above, it should be noted that various arrangements may be also be suitable. For example, any suitable combination of a fixed/variable boom elevation, fixed/variable angle cartridge, fixed/variable needle length, and/or fixed/variable pivot point may be utilized.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. An apparatus for accessing the lumen of a vessel, the apparatus comprising:
   a reusable handheld device, wherein the reusable handheld device comprises,
      an imaging device attachment, wherein the imaging device attachment is utilized to secure an image capturing instrument to the reusable handheld device;

an arm coupled to the imaging device attachment, wherein the arm provides a cartridge attachment;

a slider stop bar coupled to a needle slider, wherein the slider stop bar advances with the needle slider; and a slide stop attached to the reusable handheld device that is positioned in a sliding direction of the slider stop bar to impede advancement of the slider stop bar when it comes into contact with the slide stop; and a disposable cartridge attached to the arm of the reusable handheld device, wherein the disposable cartridge houses a needle or sheath that advances to the insertion depth indicated on the depth scale to access the lumen of the vessel, the cartridge comprises the needle slider slidably attached to the disposable cartridge, wherein the needle slider is coupled to the needle in the disposable cartridge and advancing the needle slider a predetermined amount advances a tip of the needle to the insertion depth;

a slider track receiving the needle slider, wherein when the needle slider is advanced the predetermined amount, the slider stop bar contacts the slide stop prior to contacting an end of the needle slider track to prevent the needle slider from advancing along the needle slider track beyond the predetermined amount; and a sheath slider slidably attached to the slider track of the disposable cartridge, wherein the sheath slider is coupled to the sheath in the disposable cartridge.

2. The apparatus of claim 1, wherein the reusable handheld device further comprises a thumb wheel coupled to the arm, wherein the thumb wheel is rotatable to adjust an angle of the arm, and rotation of the thumb wheel adjusts the insertion depth of the needle or sheath, and said thumb wheel is hand operated.

3. The apparatus of claim 1, wherein a body of the reusable handheld device further comprises a depth scale providing a scale indicating an insertion depth, wherein adjustment of said arm along the depth scale adjusts the insertion depth.

4. The apparatus of claim 1, wherein the disposable cartridge further comprises a lock bar that prevents movement of the needle slider and sheath slider.

5. The apparatus of claim 1, further comprising an alignment cartridge with a stylet and a stylet slider, wherein the alignment cartridge is attached to the arm of the reusable handheld device in place of the disposable cartridge, and the alignment cartridge is utilized to check a first alignment of the reusable handheld device.

6. The apparatus of claim 5, further comprising an alignment cube with at least one target vessel, wherein the reusable handheld device is placed on the alignment cube to check a second alignment of the imaging device secured to the reusable handheld device.

7. The apparatus of claim 6, wherein the alignment cube provides a first target wire and a second target wire, wherein the first target wire is arranged vertically through a center of the target vessel in the alignment cube, and the second target wire is arranged horizontally through the center of the target vessel and the second target wire intersects the first target wire.

8. The apparatus of claim 1, further comprising a screen overlay with a vertical line provided in the center of the screen overlay.

9. An apparatus for accessing the lumen of a vessel, the apparatus comprising:

a handheld device, wherein the handheld device comprises, an imaging device attachment, wherein said imaging device attachment is utilized to secure an image capturing instrument to said handheld device;

an arm coupled to said imaging device attachment, wherein said arm is adjustable to achieve various insertion depths;

a cartridge attached to said arm of said handheld device, wherein said cartridge houses a needle, sheath, or guidewire;

a needle slider for advancing and retracting the needle and a sheath slider for advancing and retracting a sheath;

a slider stop bar coupled to the needle slider, wherein the slider stop bar advances with the needle slider;

a slide stop coupled to said handheld device that is positioned in a sliding direction of the slider stop bar to impede advancement of the slider stop bar when it comes into contact with the slide stop to achieve a desired insertion depth; and a slider track receiving the needle slider and the sheath slider, wherein when the needle slider is advanced a predetermined amount, the slider stop bar contacts the slide stop prior to contacting an end of the slider track to prevent the needle slider from advancing along the slider track beyond the predetermined amount.

10. The apparatus of claim 9, further comprising a depth scale provided by a body of the handheld device, wherein the depth scale provides a scale indicating an insertion depth and adjustment of said arm along the depth scale adjusts the insertion depth.

11. The apparatus of claim 9, further comprising a lock bar that prevents movement of the needle or sheath.

\* \* \* \* \*